(12) United States Patent
Schussler

(10) Patent No.: US 8,328,962 B2
(45) Date of Patent: Dec. 11, 2012

(54) DAMPING APPARATUS, USE OF A SHAPE MEMORY ALLOY AND METHOD FOR CHANGING DAMPING CHARACTERISTICS

(75) Inventor: Kirsi Schussler, Pfinztal (DE)

(73) Assignee: ACANDIS GmbH & Co. KG, Pfinztal (DE)

( * ) Notice: Subject to any disclaimer, the term of this patent is extended or adjusted under 35 U.S.C. 154(b) by 664 days.

(21) Appl. No.: 12/088,517

(22) PCT Filed: Oct. 2, 2006

(86) PCT No.: PCT/EP2006/009552
§ 371 (c)(1),
(2), (4) Date: Jul. 17, 2008

(87) PCT Pub. No.: WO2007/039271
PCT Pub. Date: Apr. 12, 2007

(65) Prior Publication Data
US 2009/0025833 A1    Jan. 29, 2009

(30) Foreign Application Priority Data

Sep. 30, 2005  (EP) ................................... 05021542

(51) Int. Cl.
*A61F 2/44* (2006.01)
(52) U.S. Cl. .................. 148/402; 623/17.13; 623/23.53
(58) Field of Classification Search ............. 623/17.13, 623/23.53
See application file for complete search history.

(56) References Cited

U.S. PATENT DOCUMENTS 4,914,908 A * 4/1990 Sugiyama et al. ............. 60/527

(Continued)

FOREIGN PATENT DOCUMENTS

CH          684997          2/1995

(Continued)

OTHER PUBLICATIONS

White, A.A. et al., Clinical Biomechanics of the Spine, second edition, Lippincott-Raven, 1990, pp. 102-107.*
PCT Forms 101, 237, 301, 304 and 308, latest form dated Jan. 31, 2008.
Article: Shape memory alloys for medical applications; XP-000823783; Dated: Mar. 1, 1998; vol. 212 Part H; Authors: F. J. Gil and J. A. Planell.

(Continued)

*Primary Examiner* — George Wyszomierski
(74) *Attorney, Agent, or Firm* — Marshall, Gerstein & Borun LLP

(57) ABSTRACT

A damping and shock absorbing method and apparatus for permanent or non-permanent use in the human body and having a shape memory alloy material cycled through stress-strain hysteresis to dissipate energy for effective damping. A sufficiently high pre-stress is applied to the damping element(s) to ensure that the damping working range is within the superelastic cycle. The damping apparatus can work in tension or compression or both in tension and compression. Moreover, damping elements from a shape memory alloy can also work in flexion and extension as well in rotation. The damping apparatus can have a stroke and force suitable for use in the human body by the design, the structure and the chemical composition of the shape memory alloy and their pre-set properties, such as plateau stresses of the superelastic cycle depend on the ambient temperature, the force of damping elements can also be changed in-situ by changing the temperature of the damping elements. The damping elements made out of a shape memory alloy can be combined with elastic elements made out of other materials to achieve stress-strain behavior more suitable for use in the individual human body.

3 Claims, 6 Drawing Sheets

U.S. PATENT DOCUMENTS

| | | |
|---|---|---|
| 5,174,755 A | 12/1992 | Fukuda |
| 5,398,916 A | 3/1995 | Kramer et al. |
| 5,836,948 A * | 11/1998 | Zucherman et al. .......... 606/249 |
| 5,842,312 A | 12/1998 | Krumme et al. |
| 6,582,466 B1 | 6/2003 | Gauchet |
| 2002/0013586 A1 | 1/2002 | Justis et al. |
| 2003/0009223 A1 | 1/2003 | Fehling et al. |
| 2003/0149480 A1 | 8/2003 | Shadduck |
| 2006/0155279 A1* | 7/2006 | Ogilvie .......................... 606/61 |

FOREIGN PATENT DOCUMENTS

| | | |
|---|---|---|
| DE | 19727684 | 12/1998 |
| EP | 1 016 765 A2 | 7/2000 |
| JP | 01-105035 | 4/1989 |
| WO | WO 99/20358 | 4/1999 |
| WO | WO 99/67548 | 12/1999 |
| WO | WO 2004/016069 A2 | 2/2004 |
| WO | WO 2007/039271 A2 | 4/2007 |
| WO | WO 2007/039271 A3 | 4/2007 |

OTHER PUBLICATIONS

Article: Dampfungsvermogen von Formgedachtnis-Legierungen; Dated 1998; pp. 215-217; Author: P. Tautzenberger, Pforzheim.

The use of shape memory alloys for passive structural damping; XP 00493918; Dated 1995; pp. 36-41; Authors: P. Thomson, G. J. Bales and P. H. Leo.

Shape Memory Alloys as Damping Materials; XP-001021971; Dated: May 19, 1999; pp. 331-338; Authors: J. Van Humbeek and Y. Liu.

Damping characteristics of TiNi binary and ternary shape memory alloys; Dated 2003; pp. 72-78; Authors: S. K. Wu and H. C. Lin.

Utilisation of a Shape Memory Alloy; XP 000552049; Dated Oct. 1995; Authors: D. Demissy, H. Alidou and J. Pannunzio.

11039 Zeitschrift fuer Wissenschaften, ZwF [Journal of Science]; 84 (1989) No. 4, Munich Germany; Author: Dr. P. Tautzenberger, Pforzheim; Title: Damping ability of shape-memory alloys.

* cited by examiner

DAMPING APPARATUS, USE OF A SHAPE MEMORY ALLOY AND METHOD FOR CHANGING DAMPING CHARACTERISTICS

CROSS-REFERENCE TO RELATED APPLICATION

The present application claims the benefit of priority of International Patent Application No. PCT/EP2006/009552, filed on Oct. 2, 2006, which application claims priority of European Patent Application No. 05 021 542.5, filed Sep. 30, 2005. The entire text of the priority application is incorporated herein by reference in its entirety.

FIELD OF THE DISCLOSURE

The disclosure relates to a method and apparatus to passively damp shocks in the human body, and more particularly, to a spinal stabilization device which absorbs shocks to the elements of the spinal column by dissipating energy.

BACKGROUND

Back pain is one of the most widespread deceases in modern societies. After all conservative treatment (non-invasive) options such as medication, physical therapy, chiropractic or osteopathic manipulations and braces are exhausted, patients usually undergo surgical interventions such as laminectomy, discsectomy and finally fusion.

A spinal fusion surgery is designed to stop the motion at a painful vertebral segment, which in turn should decrease pain generated from the joint. New treatment options, usually called Non-Fusion Technologies or motion preservation devices, refer to implants which seek to preserve motion while stabilizing vertebra and relieving pain. There are dynamic stabilization devices (interspinous spacers or pedicle screw based), nucleus augmentation/replacement, facet replacement, annulus repair or total disc replacement.

Dynamic stabilization devices must be flexible in order to allow the spine a normal physiological motion. Thereby it is essential that adjacent levels of the treated segment are not adversely affected by the motion preservation device. Since today, spinal implants—if at all—absorb shocks only elastically (hence affecting adjacent levels), there is a need for true shock absorbing by energy dissipation in motion preservation devices.

Dynamic stabilization devices are designed to provide a certain resistance to the motion of the injured or damaged spine. Often a non-linear resistance over the range of motion in flexion/extension and tension/compression as well as rotation is desirable. Prior art solutions for dynamic stabilization devices are based on complex constructions often containing different materials. Moreover, prior art solutions do not offer any significant passive damping with energy dissipation, which is desired to prevent damage to the adjacent portions of the spine. Hence, there is a need for simple devices build from a biocompatible material with high durability that inherently offers a true damping by energy dissipation. There is moreover a need for simple devices that offer different force-deflection characteristics over their range of strain.

SUMMARY OF THE DISCLOSURE

The present disclosure provides, inter alia, such a method and apparatus for shock absorption in the spinal column and/or for dynamic stabilization in the spine.

Passive damping or shock absorption is achieved by cycling one or more damping elements built from a shape memory alloy through its stress-strain hysteresis. Energy is dissipated during the transformation of the microstructure of the material upon loading and unloading in the stress plateaus. Since the phase transformation is fully reversible even at high cycling numbers the principle is used to build damping devices in the human body. The shape memory effect has been proven for a number of metallic materials, including CuZnAl, CuAlNi, FeMgSi, FeNiCoTi and NiTi. However, until today only NiTi containing about 50.8 at % Ni, commonly referred as Nitinol, has reached a widespread use as implant material. Without limiting the scope of this disclosure which includes shape memory alloys in general, we will refer in the following only to shape memory alloys based on Nickel Titanium.

Furthermore, a NiTi based shape memory alloy phase a stress-strain behavior different from other metallic implant materials: on loading the material exhibits a high stiffness for small strain levels due to the elastic deformation of the austenitic phase, followed by a reduced stiffness for intermediate strain levels (loading/unloading plateau) and finally a large stiffness at large strain levels (elastic deformation of the martensitic phase). This provides an ideal centering force for a dynamic stabilization device with an increased resistance in the central zone of the stabilizer (elastic deformation of the Austenite), much less resistance beyond the central zone of the stabilizer (loading stress plateau) and a high resistance at the end of the range of motion (elastic deformation of the Martensite).

The phenomenon of the stress-strain hysteresis of a NiTi based shape memory alloy is used to construct a dynamic spinal stabilization device with a biased force: upon loading the stabilization device will resist forces from the adjacent spine level with a higher force (corresponding to the upper stress plateau) than the stabilization device itself will develop to the adjacent spine level (corresponding to the lower stress plateau). The biased force phenomenon of NiTi based damping device is used to avoid any detrimental impact of the spine stabilizer to adjacent spine levels.

FIG. 1 shows a systematic stress-strain curve of a shape memory alloy at a temperature T>Af where Af is the Austenite finish temperature. If Af<37° C. the material is fully austenitic at body temperature. Upon loading at low strains the austenitic material deforms firstly elastically, exhibiting a typical Hook-type straight line, known from conventional materials. At a certain stress (point A in FIG. 1) the stress-strain curve deviates from the straight line and merges into a plateau in which the stress increases only very little while the material exhibits large strains. This phenomenon is caused by the formation of Stress-Induced Martensite (SIM) and the material will exhibit large strains without any significant increase of stress until all the entire material is transformed from Austenite into Stress-Induced Martensite (point B in FIG. 1). Any loading beyond point B would first cause an elastic deformation of the Stress-Induced Martensite to point C with a significant increase of stress and beyond that (not displayed in FIG. 1) cause a plastic deformation of the material prior to rupture. Upon unloading at point B the material will first release a portion of it's elastic stress and will at point D start to transform the martensitic microstructure back to Austenite following the lower plateau line until at point E the material is fully austenitic again. During this cycle very large deformations up to ~6-8% strain (about 30 times those of conventional steel) can ideally be fully "elastically" recovered. This phenomenon is generally referred as Superelasticity or Pseudoelasticity.

During cycling through the superelastic stress-strain hysteresis and thus the formation of Stress-Induces Martensite and the formation of Austenite energy is dissipated.

The present disclosure uses this material phenomenon as a method and apparatus to absorb shocks in the human body. There are a number of advantages using this phenomenon for implantable damping elements in the human body:

First, shape memory alloys based on Nickel-Titanium (Nitinol) are biocompatible and already widely used for implants in the human body.

Secondly, the above materials exhibit the superelastic stress-strain hysteresis at body temperature.

Thirdly, compared to other damping methods, for example the visco-elastic damping method (U.S. Pat. No. 6,582,466) the force deflection hysteresis of a shape memory alloy can be utilized to build flexible implants of a simple construction with a damping capability not just in compression and tension, but also in flexion, extension as well as in rotation.

Fourthly, the reliability of a damping apparatus build from a shape memory alloy is much higher compared to other known damping methods. The stress-strain hysteresis can be performed at indefinite numbers with a high fatigue life. This is of particular importance for an implant which will be in the human body for many years.

Another advantage of a shape memory alloy is that it's damping capacity can be changed by the material (chemical composition), grain size, microstructure, porosity and defect structure in the material. Even more importantly, the level of the stress plateaus depends on the ambient temperature. Accordingly, it is possible to alter the stress-strain characteristics of a damping element out of a shape memory alloy by heating or cooling. Cooling or heating of the SMA elements would therefore result in an in-situ of the plateau stresses.

An embodiment of the damping apparatus in accordance with the present disclosure comprises at least one damping element made of a shape memory alloy and exhibiting superelastic stress-strain behavior over a predetermined range of temperatures and biasing means for applying a non-zero biasing force to the damping element.

The provision of a damping element made of a shape memory alloy and exhibiting superelastic stress-strain behavior yields desirable damping characteristics and durability. Damping can be achieved by cycling through the superelreastic stress-strain cycle, viz. the superelastic stress-strain hysteresis, of the shape memory alloy. As such, the damping apparatus provides damping by absorbing energy, e.g. during dynamic loading.

Since the superelastic stress-strain behavior of shape memory alloy is typically a function of temperature, the damping element is designed such that it exhibits superelastic stress-strain behavior over a desired range of temperatures. This range of temperatures should include the extreme temperatures expected to be encountered in the applications for which the damping element is particularly designed. As necessary, the superelastic stress-strain behavior of the damping element can be altered via appropriate choice of material and form.

The provision of biasing means for applying a non-zero biasing force to the damping element ensures that the damping element does not pass through the point of zero strain, which contributes to significantly reducing fatigue of the damping element, i.e. contributes to significantly increasing the number of damping cycles the damping element can endure before failure. In this respect, it is important to note that e.g. spinal implants such as dynamic stabilization devices must be designed to survive at least 10 million load cycles.

To exploit this positive effect that biasing has on the damping element, the non-zero biasing force preferably effects an absolute strain of at least 0.5%, at least 1% or at least 1.5% on the damping element over the desired range of temperatures. The biasing force should ensure that the absolute strain effected on the damping element is not less than the absolute strain corresponding to point E in FIG. 1. Alternatively, the biasing force will ensure that the absolute strain effected on the damping element is markedly higher than the absolute strain corresponding to point E in FIG. 1. The latter alternative ensures that the strain effected on the damping element does not fall below the absolute strain corresponding to point E in FIG. 1 even if the superelastic stress-strain behavior of the damping element should change over time, e.g. due to an unforeseen extreme change in ambient temperature or physical damage to the damping element. Naturally, the actual strain corresponding to point E in FIG. 1 depends on the material and the form of the damping element. Similarly, the actual strain corresponding to point E in FIG. 1 can differ depending on whether the damping element is subject to tension or compression. Since the damping element can be designed for operation either under tension or under compression, the term "absolute strain" is used in the specification and the claims.

While it is advantageous to chose a biasing force that will ensure that the absolute strain effected on the damping element is markedly higher than the absolute strain corresponding to point E in FIG. 1, this brings about a disadvantageous reduction in the amount of damping that can be provided by the damping element. Accordingly, the person skilled in the art will weigh the advantages of increasing the biasing force versus the disadvantages thereof when choosing a biasing force suitable for the intended application of the damping element. Accordingly, the non-zero biasing force preferably effects an absolute strain of less than 3%, less than 2.5% or less than 2% on the damping element over the desired range of temperatures. In other words, the non-zero biasing force preferably effects an absolute strain in the range of 0.5% (or, alternatively, 1% or 1.5%) to 3% (or, alternatively, 2.5% or 2%) on the damping element over the desired range of temperatures.

In a further embodiment, the biasing means for applying a non-zero biasing force serves to increase the mean strain applied to the damping element to a non-zero value. Thus, the cycling of the damping element through the superelastic stress-strain hysteresis can be effected around a mean strain of e.g. 3%, e.g. in a range between a minimum absolute strain of 1% and a maximum absolute strain of 5%.

In a further embodiment, the damping apparatus comprises limiting means for limiting a maximum strain applied to the damping element to an absolute strain of less than 8%, less than 6.5%, less than 5% or less than 4% over the desired range of temperatures. The limiting means should ensure that the absolute strain effected on the damping element is not more than the absolute strain corresponding to point B, and most certainly not more than point C, in FIG. 1. Alternatively, the biasing force will ensure that the absolute strain effected on the damping element is markedly lower than the absolute strain corresponding to point B in FIG. 1. Latter alternative ensures that the strain effected on the damping element does not exceed the absolute strain corresponding to point B in FIG. 1 even if the superelastic stress-strain behavior of the damping element should change over time, e.g. due to an unforeseen extreme change in ambient temperature or physical damage to the damping element. Naturally, the actual strain corresponding to point B in FIG. 1 depends on the material and the form of the damping element. Similarly, the actual strain corresponding to point B in FIG. 1 can differ depending on whether the damping element is subject to tension or compression.

The provision of limiting means for limiting a maximum strain applied to the damping element ensures that the damping element remains clearly within the bounds of superelastic stress-strain hysteresis, which contributes to significantly reducing fatigue of the damping element, i.e. contributes to significantly increasing the number of damping cycles the damping element can endure before failure. In conjunction with appropriately designed/dimensioned biasing means as described supra, appropriately designed/dimensioned limiting means can allow for fatigueless, viz. essentially infinite, cycling of the damping element.

As discussed above, point C marks the absolute strain at which the material—after an elastic deformation of the Martensite—begins plastic, viz. irreversible, deformation. Points B and C typically lie very close to one another along the axis of strain. Thus, a designed maximal strain on the damping element equal to the absolute strain corresponding to point B in FIG. 1 bears the danger of becoming a strain in excess of an absolute strain corresponding to point C in FIG. 1, e.g. in exceptional/extreme circumstances or if the superelastic stress-strain behavior of the damping element, as discussed above, should change over time. Accordingly, the provision of limiting means for limiting a maximum strain applied to the damping element moreover ensures that the damping element does not undergo a plastic deformation that, invariably, would undesirably and irreversibly alter the functional characteristics of the damping element.

In a preferred embodiment, the damping apparatus is configured and adapted for implantation in a living creature, in particular in a human body. In this respect, it has been determined that a damping apparatus as described herein exhibits characteristics that make it particularly suitable for use as an implant.

In a preferred embodiment, the damping apparatus is configured and adapted for intervertebral implantation in a human spine. As described in detailed infra, the stress-strain characteristics of the damping apparatus in accordance with the present disclosure provide a highly desirable, if not ideal, centering force that makes the damping apparatus particularly suitable for dynamic stabilization of and/or for shock absorption in a human spine. Accordingly, the damping apparatus of the present disclosure can be configured and adapted as a dynamic (spinal) stabilization device or as an intervertebral spacer element.

The damping apparatus of the present disclosure can equally find use as a dynamic stabilization device and/or shock absorber for artificial joints such as hip implants.

In a preferred embodiment, the aforementioned desired range of temperatures is the range of body temperatures of living human bodies. The damping apparatus is preferably designed to exhibit its most desirable characteristics in the range of "normal" body temperatures of healthy humans. This provides for the desired superelastic stress-strain behavior, in particular when the damping apparatus is used as a human implant. Naturally, where the damping apparatus is intended for use as an implant in other living creatures, the desired range of temperatures must be chosen appropriately.

In a further embodiment, the damping element is made of a binary NiTi shape memory alloy, for example Ti-50.8 at % Ni, or a ternary NiTi shape memory alloy. Such alloys have been found to have characteristics that make them particularly suitable for use in the damping element of the present disclosure. The cyclic fatigue behavior of NiTi differs from that of conventional implant materials such as Ti-6Al-4V or stainless steel.

In a further embodiment, the damping element exhibits a symmetrical response or an approximately symmetrical response under compression vs. tension. Shape memory alloys, especially cold-worked NiTi materials, typically respond differently under tension than they do under compression. This asymmetrical response can be countered, at least in part, by appropriate casting and/or heat treatment of the damping element.

In a further embodiment, the damping element comprises a first damping element that is configured and adapted to function as a compression spring and a second damping element that is configured and adapted to function as a tension spring. Such an embodiment avoids a reverse cyclic loading of the device, which would undesirably decrease the fatigue life of the damping apparatus.

DETAILED DESCRIPTION OF THE PREFERRED EMBODIMENT

Figure 1:
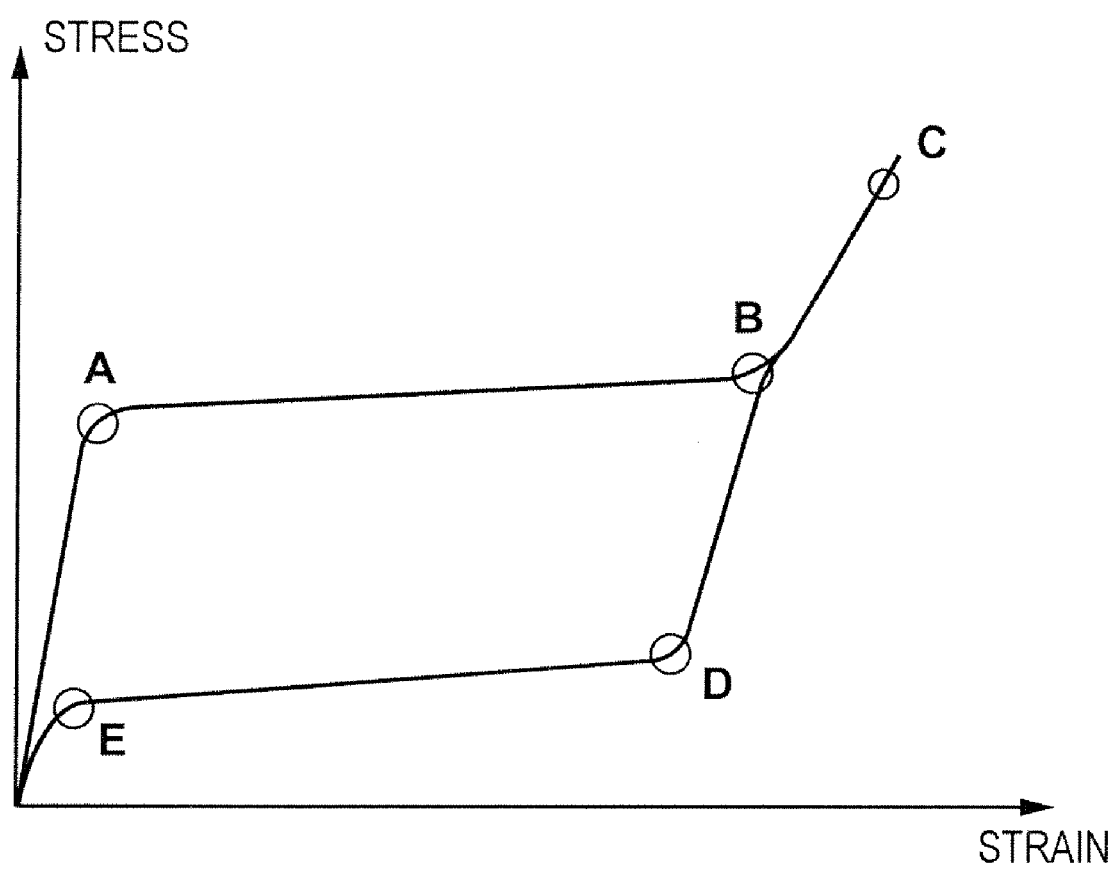
FIG. 1 shows the general stress-strain behavior of a shape memory alloy on loading and unloading with distinctive stress plateaus.
Figure 2:
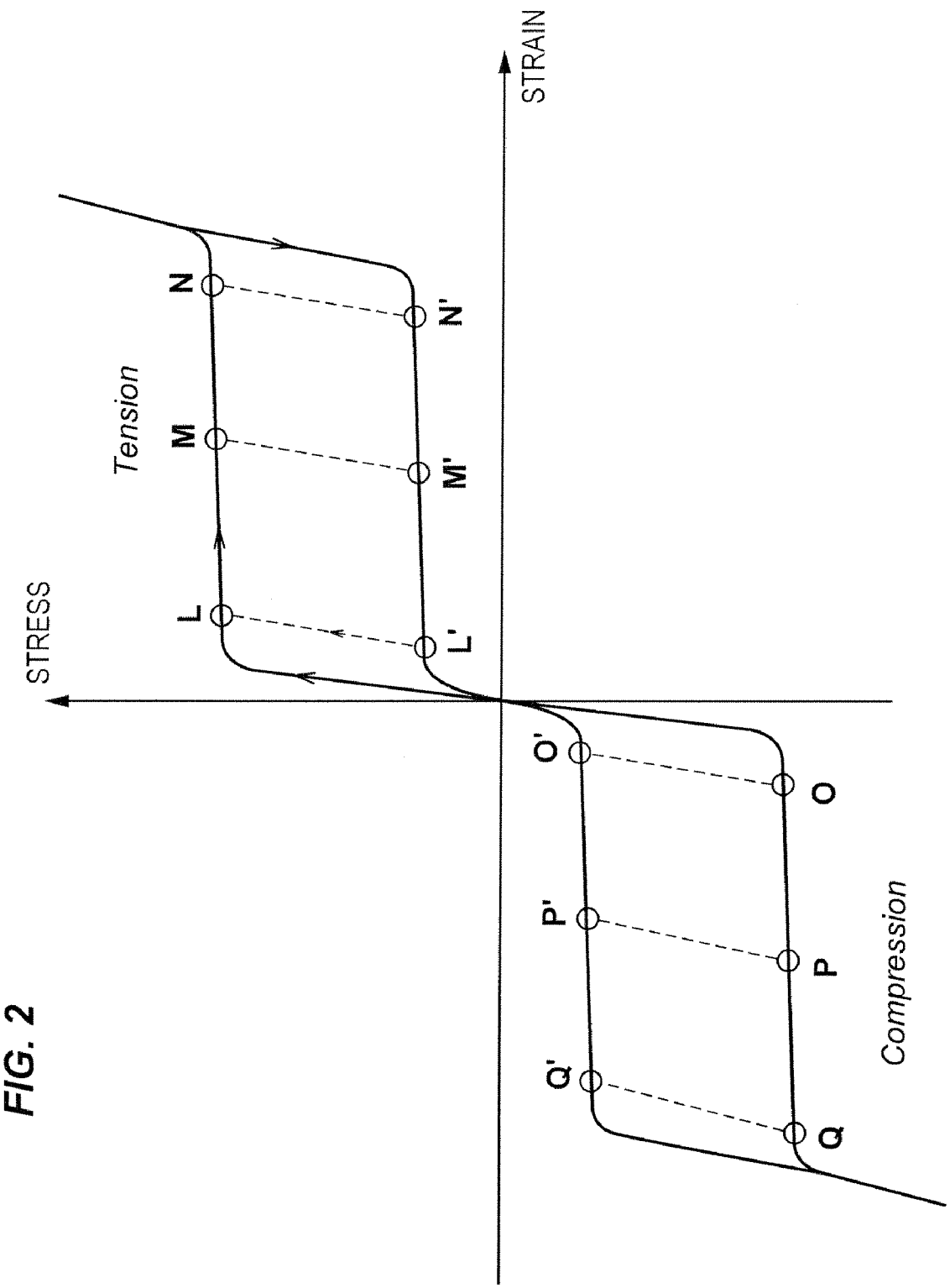
FIG. 2 illustrates the schematic stress-strain behavior of a damping element constructed out of a SMA tension and compression spring.
Figure 3:
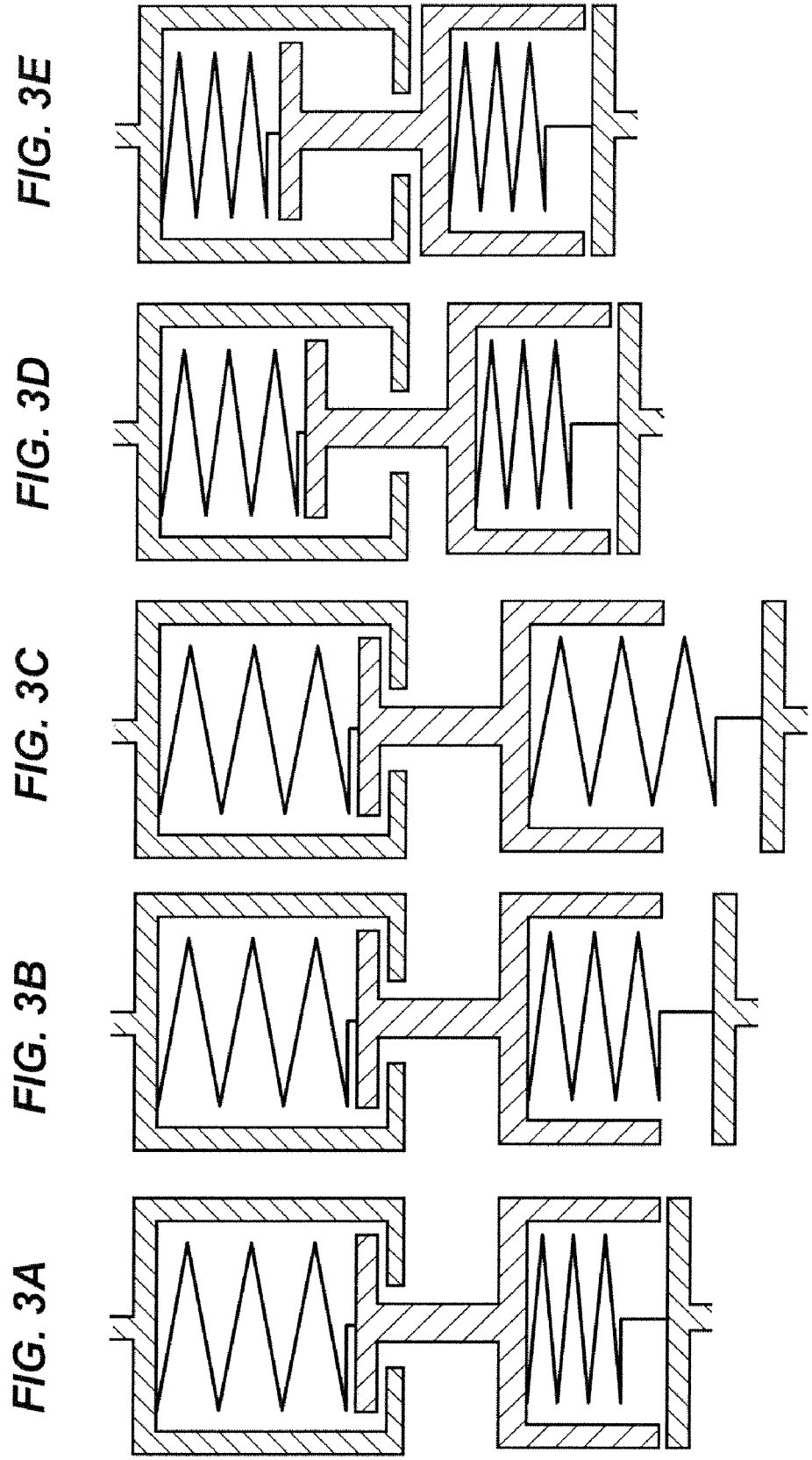
FIG. 3 illustrates the plan view of a damping element device built from a combined SMA tension and compression spring.

FIG. 3 shows a damping element consisting out of a SMA tension and a compression spring. The upper spring is the compression spring, the lower spring is the tension spring. Both springs are pre-strained in order to assure that tension and compression occur only in the region of the plateaus. FIG. 3a shows the damping element prior to any loading. In this condition the force of the compression spring correlates to the point 0 or 0' on the stress strain curve in FIG. 2 depending on the loading or unloading condition. The tension element rests at point L (loading) or L' (unloading).

Upon the first tension of the damping element (FIG. 3b) the stress-strain behavior of the tension spring follows the curve L'-L-M (FIG. 2). The translation from L' to L basically occurs with very little strain but a significant increase in stress (force). After reaching the stress of the superelastic loading plateau the spring strains to point M without any further significant increase of the stress (force). In case that no further tension occurs and the tension spring follows the unloading cycle from M to M' and finally to L'. By doing so the energy dissipated within this loop corresponds to the area of the rectangular L'-L-M-M'.

The case of further tension (beyond point M in FIG. 4) is displayed in FIG. 3c: the tension spring is strained to point N (FIG. 2) of the stress-strain curve. Any further tension beyond point N should be hampered, either by the natural increase of the stress beyond the loading plateau stress or by constructive means of the spring elements. Upon relief of the stress the tension spring first follows the unloading plateau stress to point N' and thereafter the unloading plateau to those strains which correspond to the applied stress levels up to the point L' which defines the pre-strained tension of that spring.

It is important to point out that due to the hysteresis the SMA damping element will resist forces applied to it with a higher force (corresponding to the upper stress plateau) than it will develop to the human body (corresponding to the lower stress plateau).

Since the damping element consists out of a tension and a compression spring, damping (energy dissipation) occurs also in compression. Moderate compression is displayed in FIG. 3d while the tension spring is not activated. Upon compression the compression spring moves it's stress-strain characteristics from point O' to O and furthermore to point P (FIG. 2). If the tics will follow the line from P to P' and thereafter to strains corresponding stresses of the unloading up to the pre-strained condition (point O'). the damping (energy dissipation) corresponds to the area of the rectangular made between O'-O-P-P' (FIG. 2). The case of a maximal compression of the compression spring is shown in FIG. 3e: in this case the spring is at maximum allowable strains corresponding to point Q (FIG. 2). Any further compression is hampered either by the natural increase of the stress after the loading stress plateau or must be by constructive means of the spring element. If the compression is released the stress-strain behavior follows the line from Q to Q' and thereafter the unloading plateau to strains corresponding to the remaining compression stresses. Again the amount of damping (energy dissipation) corresponds to the area build by the rectangular of the stress-strain hysteresis.

Figure 4:
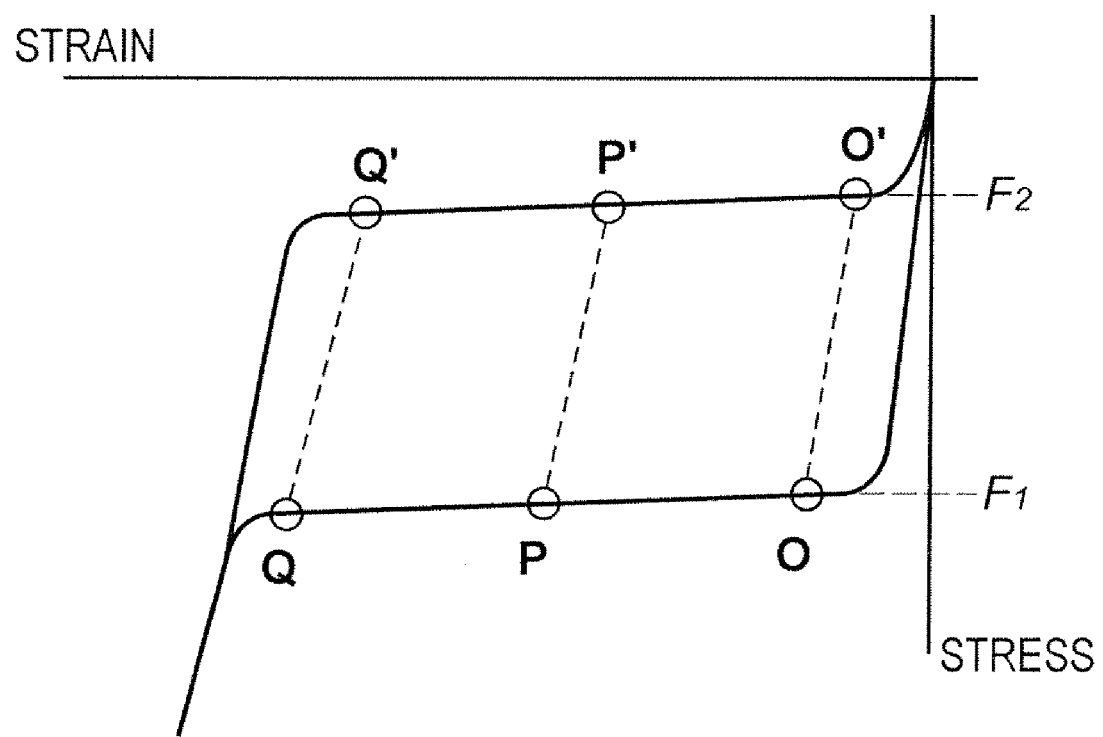
FIG. 4 illustrates the schematic stress-strain behavior of a damping element constructed from a SMA compression spring.
Figure 5A:
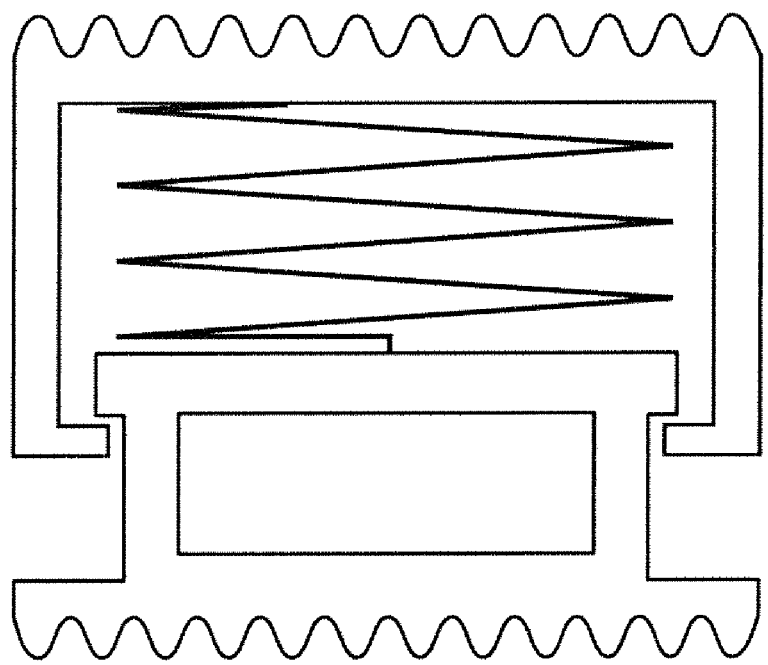
FIG. 5 illustrates the plan view of a SMA damping element constructed from a compression spring.
Figure 5B:
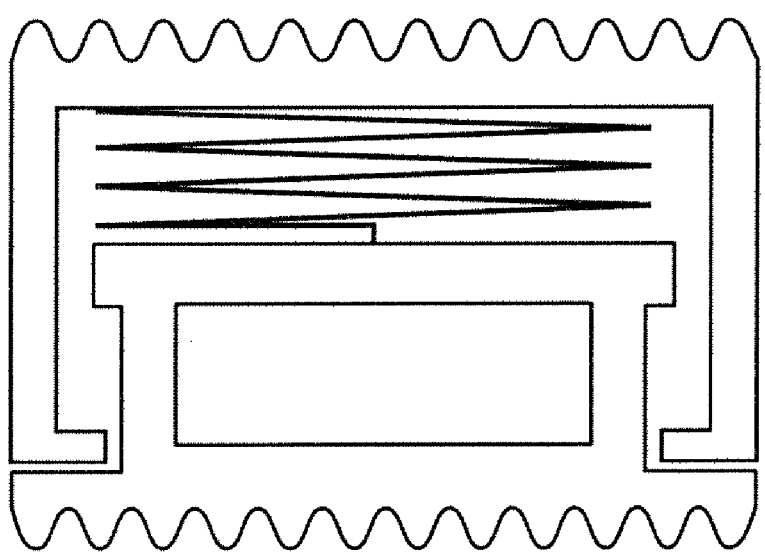

In one embodiment of the disclosure the damping device consists only out of a compression element FIG. 5. the stress-strain behavior of the compression element is displayed within the general stress-strain behavior of a shape memory alloy in FIG. 4. The compression element is pre-strained to at least point O of the stress plateau. The pre-straining can occur by either constructive means (for example as indicated in FIG. 5a) or alternatively, by applying sufficient a force during application in the human body. During a compression cycle the damping behavior (energy dissipation) is achieved by cycling the compression element within a rectangular within the points O-P-Q-Q'-P'-O'. the pre-strained damping element in FIG. 5a would be at point O' upon an unloading condition in FIG. 4. On compression the damping element develops a relatively high force F1 to reach the upper stress plateau (point O) before it will be significantly strained. Once the stress plateau is reached only very little additional stress (force) is needed in order to cause compression of the damping element. Full compression of the damping element is reached at point Q in FIG. 4, corresponding to FIG. 5b. Upon relief of the compressive force the stress-strain behavior of the damping element reduces it's compression following the unloading curve Q'-P'-O': it is important to note that—due to the stress-strain hysteresis—upon unloading a much lower force F2 form the compression element to the human body is developed compared to force F1 element itself resists the compressive force. It is understood that the compression of the damping beyond point Q will be avoided either by further increase of stress due to the elastic deformation of the Martensite or has to be done by constructive constraints.

It should also be mentioned that any pre-straining of the damping element can also be achieved by using the natural loads applied by the human body. In this case it can be of advantage to set the pre-strain to point P or P' of the stress-strain curve.

It is another embodiment of the disclosure to use the specific stress-strain characteristics of a NiTi based SMA alloy to provide non-linear resistance for dynamic stabilization of the spinal column. High stiffness for small strain levels due to the elastic deformation of the austenitic phase and a reduced stiffness for intermediate strain levels (loading/unloading plateau) provide an ideal centering force for a dynamic stabilization device with an increased resistance in the central zone of the stabilizer (corresponding to the neutral zone of the spine) and much less resistance beyond the central zone of the stabilizer which is essential for a dynamic stabilization device (PANJABI, WO 04098452A2). In addition to that, the stress increase of NiTi based SMA's after the stress-plateaus due to the elastic deformation of the Martensite can be used to provide a high resistance at the end of the range of motion.

Figure 6:
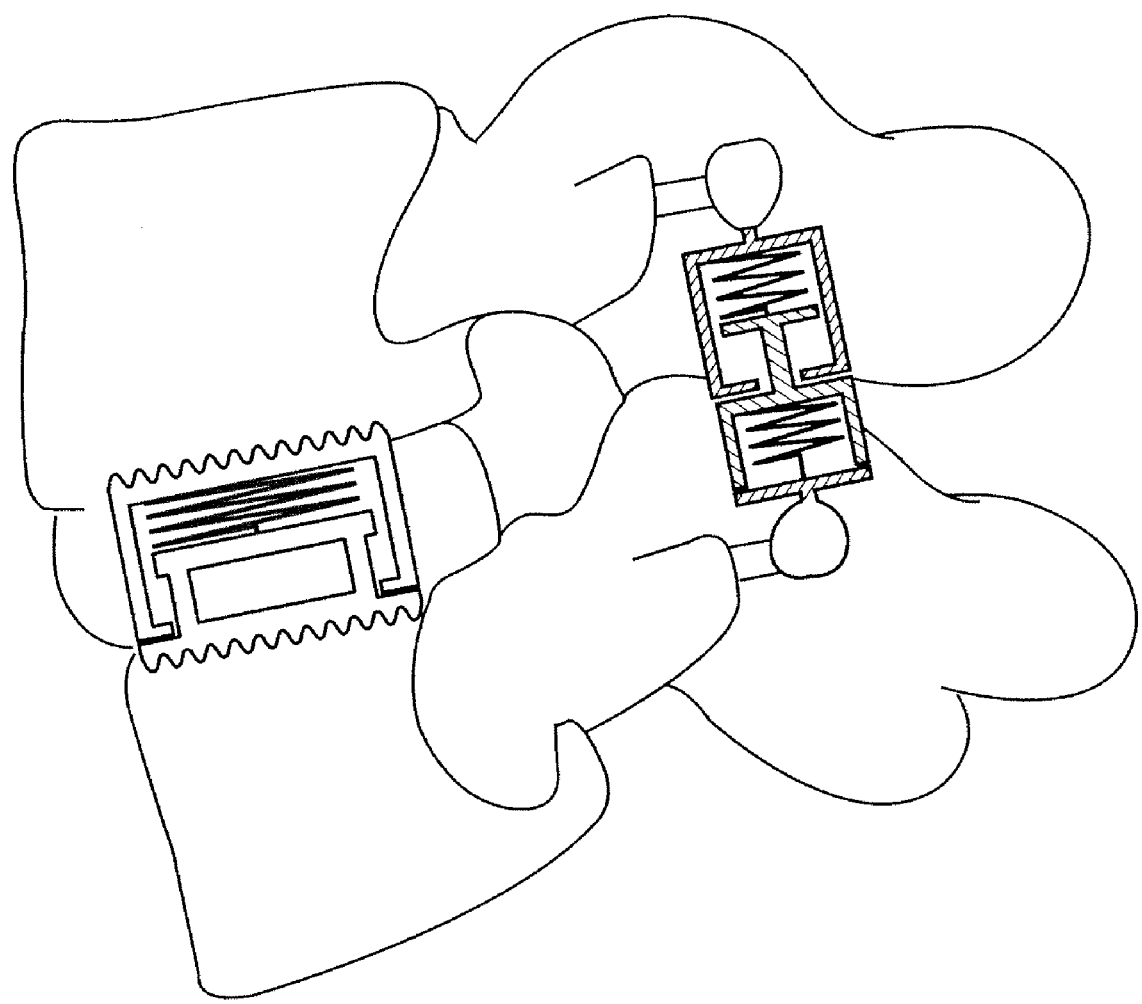
FIG. 6 shows a side view of two adjacent vertebrae with a SMA damping element space holder in between and a dynamic stabilization device based on SMA damping elements fixed by pedicle screws.

FIG. 6 shows an application of the first two embodiments of the disclosure, which is the application of a NiTi based SMA damping element as a space holder between two adjacent vertebrae and a dynamic stabilization device fixed by pedicle screws on the spinal column. The advantage of the SMA space holder which can also be constructed with an open structure to inject bone mass is in contrast to the prior art is that true damping is provided leading to the dynamic stabilization device which in addition will provide an ideal centering force and a stress-strain characteristic with an increase resistance in the central zone and less resistance beyond the central zone of the spine.

Briefly summarized, the present disclosure relates to a damping and shock absorbing method and apparatus for permanent or non-permanent use in the human body consists out of a shape memory alloy material which is cycled through the stress-strain hysteresis to dissipate energy for an effective damping. A sufficiently high pre-stress is applied to the damping element(s) to ensure that the damping working range is within the superelastic cycle. The damping apparatus can be designed to work in tension or compression or—by combination of compression and tension elements—both in tension and compression. Moreover, damping elements from a shape memory alloy can be designed to work also in flexion and extension as well in rotation. The damping apparatus can be designed to have a stroke and force suitable for use in the human body by the design, the structure and the chemical composition of the shape memory alloy and their pre-set properties, such as plateau stresses and transformation temperature. Since plateau stresses of the superelastic cycle depend on the ambient temperature, the force of damping elements can also be changed in-situ by changing the temperature of the damping elements. The damping elements out of a shape memory alloy can be combined with elastic elements out of other materials to achieve stress-strain behavior more suitable for use in the individual human body.

Particularly preferred features/embodiments of the disclosure, to the respect not already reflected in the claims, can be summarized as follows:

There is a damping apparatus for absorbing energy during dynamic loading in the human body having at least one shape memory alloy damping element exhibiting a superelastic stress-strain behavior at body temperature, and where the damping element is pre-strained within the apparatus and is adapted to achieve damping by cycling—at least partly—through the superelastic stress-strain cycle.

There is a method and apparatus for shock absorption in the spinal column, and more particularly for a dynamic stabilization of the spine, having at least one shape memory alloy damping element exhibiting a superelastic stress strain behavior at body temperature, and where the damping element is pre-strained within the apparatus to achieve damping by cycling—at least partly—through the stress-strain cycle and to assure the desired durability behavior.

Also, regarding the above method and apparatus, there is pre-straining of the device that occurs in the range between 1% strain and 5% strain, and preferably between 1% strain and 3% strain.

Then, for the above apparatus, there is the shape memory alloy which has a binary NiTi shape memory alloy (for example Ti-50.8 at % Ni) or a ternary NiTi shape memory alloy.

Then also, for the above apparatus, where the damping element is produced by casting and heat treatment to overcome unsymmetrical response in compression vs. tension of cold worked NiTi materials.

Also, for the above apparatus, the shape memory damping element can be springs, particularly NiTi springs.

Then, for the apparatus, there can be at least two damping elements, with one functioning as a compression spring and the other as a tension spring.

Further, there is a dynamic stabilization device and intervertebral spacer element for the spinal column, as formed of the above apparatus.

Then, there is a dynamic stabilization device for artificial joints, such as hip implants, as formed by the above apparatus.

Also, there is the of shape memory alloy damping devices for dynamic stabilization devices and intervertebral spacer element for the spinal column and/or for dynamic stabilization devices for artificial joints, such as hip implants.

Also, there is the in-situ change of damping characteristics by changing the temperature of the SMA damping element.

Further, there is a shape memory alloy self centering dynamic stabilization device with an increased resistance in the central zone of the stabilizer (corresponding to the neutral zone of the spine) and with much less resistance beyond the central zone of the stabilizer.

Further yet, there is a intervertebral spacer and dynamic stabilization device, respectively built from a shape memory alloy which will resist outside forces with a higher force (corresponding to the upper stress plateau) than it will itself develop to the adjacent spine level (corresponding to the lower stress plateau).

Also, there is a method for absorbing energy during dynamic loading in the human body, including the step of providing at least one shape memory alloy damping element exhibiting a superelastic stress-strain behavior at body temperature, where the damping element is pre-strained within the apparatus and adapted to achieve damping be cycling—at least partly—through the superelastic stress-strain cycle.

Also, there is a method for a spinal implant, including the step of providing at least one shape memory alloy damping element exhibiting a superelastic stress-strain behavior at body temperature, wherein the damping element is pre-strained within the apparatus and adapted to achieve damping be cycling—at least partly—through the superelastic stress-strain cycle.

The invention claimed is:

1. A damping apparatus for absorbing shocks in the human body, comprising: at least one damping element made of a shape memory alloy and exhibiting superelastic stress-strain behavior over a predetermined range of temperatures, and biasing means for applying a non-zero biasing force to said damping element, wherein said non-zero biasing force effects an absolute strain of 0.5% to 3% on said damping element over said predetermined range of temperatures, and wherein said damping element exhibits a symmetrical response under compression vs. tension.

2. A damping apparatus, comprising: at least one damping element made of a shape memory alloy and exhibiting superelastic stress-strain behavior over a predetermined range of temperatures, and biasing means for applying a non-zero biasing force to said damping element, wherein the damping apparatus absorbs shocks in a human body and wherein said damping element exhibits a symmetrical response under compression vs. tension.

3. A damping apparatus for absorbing shocks in the human body, comprising: at least one damping element made of a shape memory alloy and exhibiting superelastic stress-strain behavior over a predetermined range of temperatures, the damping element adapted to achieve damping through a superelastic stress-strain cycle, wherein the damping element exhibits a symmetrical response under compression vs. tension.

* * * * *